United States Patent [19]

Behringer et al.

[11] 4,268,437

[45] May 19, 1981

[54] CONTINUOUS DIAZOTIZATION OF AMINES

[75] Inventors: Hartmut Behringer; Kurt Karrenbauer, both of Erftstadt, Fed. Rep. of Germany

[73] Assignee: Hoechst Aktiengesellschaft, Fed. Rep. of Germany

[21] Appl. No.: 47,698

[22] Filed: Jun. 12, 1979

[30] Foreign Application Priority Data

Jun. 12, 1978 [DE] Fed. Rep. of Germany ....... 2825655

[51] Int. Cl.³ .......................................... C07C 113/04
[52] U.S. Cl. ..................................................... 260/141
[58] Field of Search .................................... 260/141 P

[56] References Cited

U.S. PATENT DOCUMENTS

| | | | |
|---|---|---|---|
| 3,117,954 | 1/1964 | Hupper | 260/141 |
| 3,423,391 | 1/1969 | Kindler et al. | 260/141 |

FOREIGN PATENT DOCUMENTS

| | | | |
|---|---|---|---|
| 191399 | 8/1957 | Austria | 260/141 |
| 1226594 | 10/1966 | Fed. Rep. of Germany | 260/141 |
| 2617913 | 11/1976 | Fed. Rep. of Germany | 260/141 |
| 812368 | 4/1959 | United Kingdom | 260/141 |
| 844062 | 8/1960 | United Kingdom | 260/141 |

*Primary Examiner*—Floyd D. Higel
*Attorney, Agent, or Firm*—Connolly and Hutz

[57] ABSTRACT

The invention provides a process for the continuous diazotization of primary aromatic amines by reacting an aqueous solution or suspension of the amine in a mineral acid with an aqueous sodium nitrite solution. To this end, the lower portion of a cylindrical diazotization vessel placed in upright position is fed continuously with an aqueous mineral acid solution or suspension of a diazotizable primary aromatic amine. At the same time, the vessel is fed, via one or more inlets arranged one above the other so as to open laterally thereinto, with an aqueous sodium nitrite solution, the amine and nitrite being used in stoichiometric proportions, or the nitrite being used in a stoichiometric deficiency and the acid being used in an excess of about 1 to 3 equivalents per amine equivalent in the mineral acid solution. The resulting mixture is reacted while producing a laminar flow of liquid matter at temperatures of about 5° to 30° C. Next, reaction mixture is removed, in accordance with the diazotization velocity of the particular amine used, from the upper portion of the diazotization vessel at a place where the reaction mixture is substantially free from nitrous acid, said place being situated in the vessel at a level which is the higher the lower the diazotization velocity of the amine used. The reaction mixture removed is finally filtered and diazonium salt-containing solution is delivered to a sojourn zone.

8 Claims, 1 Drawing Figure

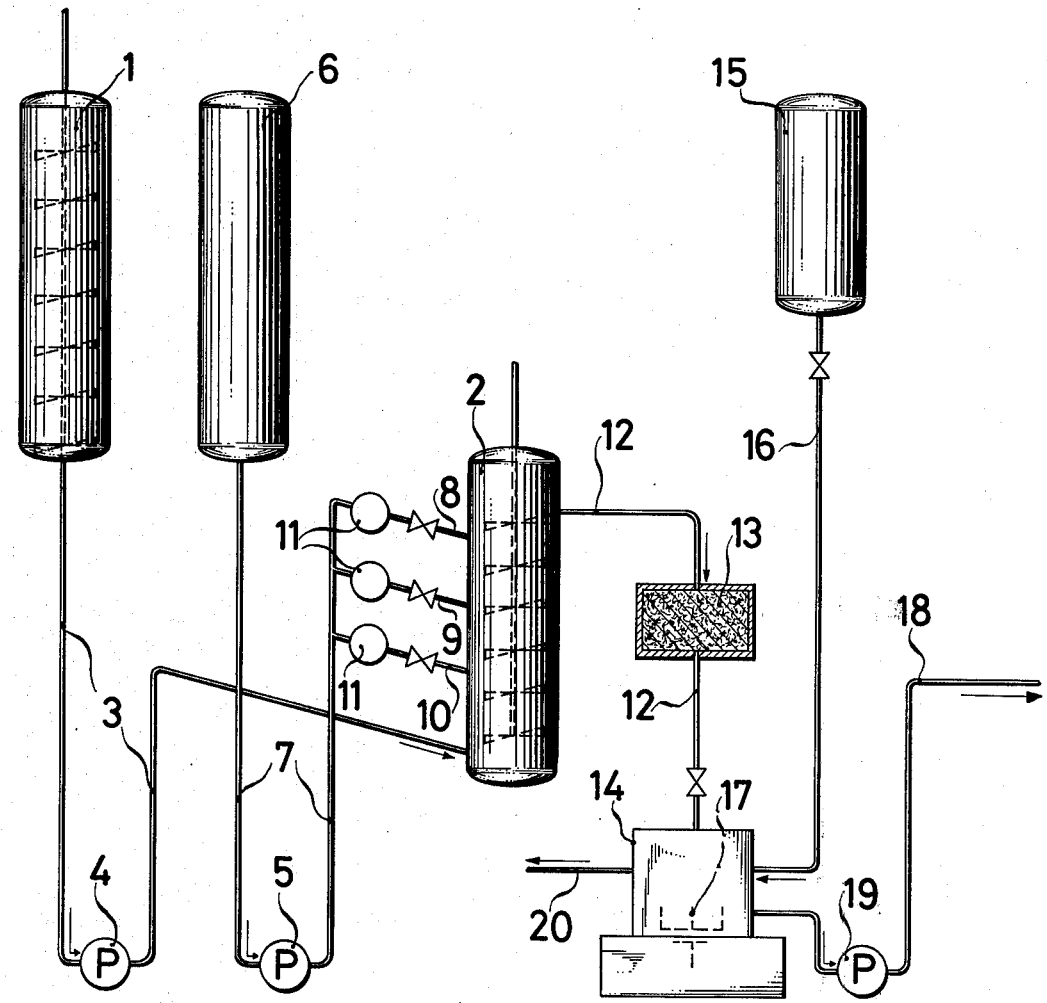

CONTINUOUS DIAZOTIZATION OF AMINES

This invention relates to the continuous diazotization of amines.

The diazotization of primary aromatic amines so as to obtain diazonium salts is of considerable commercial interest as regards the production of azo dyestuffs.

Primary aromatic amines are normally diazotized discontinuously. To this end, the amine is placed in an agitator-provided vessel and dissolved or suspended therein in an aqueous mineral acid, e.g. hydrochloric or sulfuric acid, the mineral acid being commonly employed in an excess of 2.5 to 3 equivalents per equivalent of amine. Next, the solution or suspension is admixed with an aqueous concentrated sodium nitrite solution for as long as necessary to reach the point of equivalence. By the addition of ice, the reaction mixture is maintained at a temperature of about 0° to 5° C. The resulting diazonium salt or its aqueous solution is generally filtered and used in coupling reactions for making azo dyestuffs.

This is a commercial process which suffers from serious deficiencies in respect of the following points: The space/time-yield is unsatisfactory. This is a result of the fact that use is made of the agitator-provided vessel (a) for dissolving or suspending the amine in the aqueous mineral acid, (b) for effecting the diazotization reaction, and (e) for storing the resulting diazonium solution therein until work-up. In other words, the vessel is at least temporarily not available for effecting further diazotization reactions therein, which is disadvantageous. A further technically adverse effect of discontinuous diazotization resides in the relatively long periods over which the diazonium salt, once it has been formed, is allowed to remain in the agitator-provided vessel until the reaction is terminated. It is well known in the art that diazonium salts are more or less readily decomposable and that the quality of secondary products made therefrom is seriously impaired if the diazonium salts actually decompose. It is therefore highly desirable for the residence or storage period of diazonium salt solutions in the diazotization vessel to be kept constant and as short as possible, or for that period to be at least variable without blockading the use of the vessel for diazotizing a fresh batch.

A process for the continuous diazotization of amines has already been described in German Pat. No. 960 205, wherein a diazotizable amine, which may be used in salt form and in admixture with a suitable solvent, is introduced continuously and jointly with a diazotizing agent and with or without one or more acids as diluents into a precooled solvent or diluent, in which reaction mixture gradually concentrates as the reaction proceeds, the introduction of the various reactants being controlled depending on the composition selected for the final product which is continuously removed.

This prior process does, however, not favorably compare with the discontinuous diazotization inasmuch as it is necessary over the entire reaction period to use a diazonium salt solution with an excess of nitrous acid therein, which promotes the decomposition of the diazonium salt and impairs the quality of secondary products made therefrom. Last but not least, the process just described is rendered disadvantageous by the fact that it is necessary for the bulk of the diazonium salt solution to be recycled so that the tendency of the diazonium salt to undergo decomposition is even increased. It is therefore an object of the present invention to provide a process for the continuous diazotization of diazotizable amines in good yields, which avoids the technically adverse effects described hereinabove.

The present invention relates more particularly to a process for the continuous diazotization of primary aromatic amines by reacting an aqueous solution or suspension of the amine in a mineral acid with an aqueous sodium nitrite solution, which comprises: supplying continuously the lower portion of a cylindrical diazotization vessel placed in upright position with an aqueous mineral acid solution or suspension of a diazotizable primary aromatic amine and supplying the vessel simultaneously, via one or more inlets arranged one above the other so as to open laterally thereinto, with an aqueous sodium nitrite solution, the amine and nitrite being used in stoichiometric proportions, or the nitrite being used in a stoichiometric deficiency and the acid being used in an excess of about 1 to 3 equivalents per amine equivalent in the mineral acid solution; reacting the resulting mixture with agitation and producing a laminar flow of liquid matter at temperatures of about 5° to 30° C.; removing reaction mixture, in accordance with the diazotization velocity of the particular amine used, from the upper portion of the diazotization vessel at a place where the reaction mixture is substantially free from nitrous acid, said place being situated in the vessel at a level which is the higher the lower the diazotization velocity of the amine used; filtering the reaction mixture removed and delivering diazonium salt-containing solution to a sojourn vessel.

The process of the present invention can be modified in various ways depending on the diazotization velocity of the particular aromatic amine used. In all those cases in which use is made of an amine which rapidly undergoes diazotization, it has been found good practice, for example, to introduce the aqueous sodium nitrite solution exclusively into the diazotization vessel through the lowermost inlet possible.

On the other hand, in all those cases in which the amine to be diazotized is one which undergoes diazotization at a reduced velocity, it is good practice to introduce the aqueous sodium nitrite solution into the diazotization vessel, through a plurality of inlets disposed at different levels, the sodium nitrite solution being admitted through the individual inlets in quantities decreasing from above to below so as to have a minor excess proportion of nitrous acid just in the reaction mixture formed within the region of the uppermost inlet. In the case just described, it is also possible to supply the diazotization vessel with a stoichiometric deficiency (with respect to the amine) of aqueous sodium nitrite solution, to filter off unreacted amine from the reaction mixture removed, and to recycle the filter residue to the diazotization vessel.

A further preferred feature of the present invention provides for the amine to be diazotized at a temperature of 10° to 20° C., irrespective of the nature of the particular amine concerned. To ensure reliable operation, it is an important requirement for the reaction mixture to contain, at the discharge place from the diazotization vessel, some minor excess proportion of nitrous acid, which is recognizable by spot reaction on potassium iodide starch paper, and which is an index of the completeness of the reaction. The present process permits unreacted amine to be post-diazotized outside the diazotization vessel, namely in the sojourn vessel placed downstream thereof, by admixing it with aqueous sodium nitrite solution, and thus provides for the diazotization to be controlled.

Finally, the present process permits the quality of the diazonium salt solution and azo dyestuffs which are made therefrom to be influenced in reproducible manner by varying the residence time of the reaction mixture in the sojourn vessel. Generally, the residence time for diazonium salt solutions made from readily diazotizable amines is about 1 to 10 minutes, and for those which are made from difficultly diazotizable amines is about 10 to 30 minutes.

The process of the present invention will now be described in greater detail with reference to the accompanying drawing.

An aqueous solution or suspension of a primary aromatic amine and mineral acid in an agitator-provided vessel 1 is delivered by means of a dosing pump 4 and via a conduit 3 to an agitator-provided diazotization vessel 2. At the same time, a predetermined quantity of aquous sodium nitrite solution coming from a reservoir 6 is introduced by means of a pump 5 via a conduit 7 and supply inlets 8, 9 and 10 into the diazotization vessel 2, the quantity supplied being controlled by a rotameter 11. The diazotization vessel 2 is provided with a cooling jacket (not shown in the drawing) permitting the reaction mixture to be cooled. The blades of the agitator in the diazotization vessel 2 are arranged so as to ensure a good mixing effect in the plane which runs transversely to the agitator axis, the agitating velocity being sufficient to produce a laminar liquid flow in the direction of the agitator axis. As a result of the laminar flow conditions which are established inside the diazotization vessel 2, it is possible for the diazonium salt to remain over a defined period of time in the vessel, the residence time depending exlusively on the dimensions of the diazotization vessel and the quantity of liquid which is admitted thereto per unit time.

Reaction mixture issuing through a conduit 12 is filtered in a filtering device 13 and collected in a sojourn vessel 14.

In the event of undissolved unreacted amine being contained in the aqueous diazonium salt solution collected in the sojourn vessel 14, it is possible to subject the solution to post-diazotization in the sojourn vessel 14 by introducing aqueous sodium nitrite solution thereinto, the latter solution coming from a tank 15 and travelling through a conduit 16. A magnetic agitator 17 is used for thoroughly mixing the material in the sojourn vessel 14. The final diazonium salt solution is removed through a conduit 18 by means of a pump 19. Conduit 20 can be used for operation of the filter 13 under vacuum, if desired or necessary.

The process of the present invention compares favorably with the prior art in respect of the following points: As a result of the short residence time of the reaction mixture in the diazotization vessel, it is possible in the present process to effect the diazotization of the amines while cooling with water, without the need to use ice as in the prior art methods. The use of the nitrite in a stoichiometric deficiency and the step of recycling unreacted amine, which is not separated in the filter, to the diazotization vessel has turned out beneficial in the diazotization of difficultly diazotizable amines. More specifically, the diazonium salt remains in the reactor over a short while only, and the process is easy to control just by regulating the quantity of nitrite admitted to the reactor.

Last but not least, it is possible by the arrangement of a sojourn vessel downstream of the diazotization vessel to regulate the residence time of the diazonium salt solution, and in this manner reproducibly to influence under control the quality of the diazonium salt solution and/or azo dyestuffs which are made therefrom.

EXAMPLE 1

253 g (1 mol) of 3,3'-dichlorobenzidine was suspended in vessel (1) in 2500 ml of water and the resulting suspension was stirred for 15 minutes. Next, it was admixed with 510 ml of hydrochloric acid of 31 weight % strength, and the whole was stirred for a further 15 minutes. By means of dosing pump (4), the suspension was pumped continuously within 1 hour into the base portion of the cylindrical diazotization vessel (2) which was 4 cm wide and 25 cm high. At the same time, a 20 weight % aqueous sodium nitrite solution coming from reservoir (6) was continuously introduced through inlet (10) into the diazotization vessel (2); the nitrite solution was used in a quantity sufficient for the diazonium salt solution issuing from the diazotization vessel (2) to contain a minor excess proportion of nitrite. 600 ml or 2 mols of sodium nitrite solution was consumed. The temperature inside the diazotization vessel was maintained at about 15° C. by means of water. A clear bright yellow diazonium salt solution was obtained after filtration. The conversion rate was 100 %.

EXAMPLE 2

304 g (2 mols) of 3-nitro-4-aminotoluene, 850 ml of water and 500 ml of hydrochloric acid of 31 weight % strength were stirred together for 15 minutes in the vessel (1). By means of dosing pump (4), the suspension so obtained was pumped continuously within 1 hour into the base portion of the diazotization vessel (2). At the same time, the diazotization vessel (2) was continuously supplied, through inlets (8, 9 and 10) with a quantity of a 20 weight % sodium nitrite solution necessary for the reaction mixture to remain free from nitrite in excess within the region of inlets (9) and (10) and to contain some minor excess proportion of nitrite within the region of inlet (8). The bulk of nitrite solution was introduced into the base portion, a small quantity was introduced into the center protion, and a minor quantity was introduced into the head portion of the diazotization vessel (2). A temperature of about 20° C. was maintained inside the vessel (2) by means of cooling water. A clear reddish to bright violet diazonium salt solution was obtained downstream of the filter. The conversion rate was 100%.

EXAMPLE 3

The procedure was as described in Example 2, but a temperature of only 15° C. was maintained inside the diazotization vessel (2). In addition to this, only 90 weight % (based on the quantity used in Example (2) of sodium nitrite solution was used, and the solution was introduced into the diazotization vessel exclusively through the lowermost inlet (10). 3-nitro-4-amino-toluene in excess was separated from the reaction mixture in filtering device (13), recycled to the vessel (1) and used for preparation of the next batch, which was composed of 90% of fresh and 10% of recovered and recycled 3-nitro-4-aminotoluene.

Recovered amine was recycled nine times, without any adverse effect on the quality of the diazonium salt. Amine obtained as filter residue after the 10th cycle was discarded to remove impurities. The filtrate was a diazonium salt solution brown colored by 3-nitro-4-aminotoluene which was dissolved therein. The solution was postdiazotized in the sojourn vessel (14) by admixing it with a minor quantity of sodium nitrite solution. The diazonium salt solution turned reddish-violet. After having been allowed to remain in the sojourn vessel (14) over 15 minutes, it was taken therefrom for work up.

EXAMPLE 4

The procedure was as described in Example 3, but the residence time of the diazonium salt solution in sojourn vessel (14) was once reduced to 5 minutes and once increased to 30 minutes. The different residence times resulted in the formation of qualitatively different diazonium salts as was evidenced by the tint of the azo dyestuffs made from the respective diazonium salt.

EXAMPLE 5

345 g (2 mols) of 4-chloro-2nitraniline was made into a paste with 136 ml of water and the paste was admixed with 520 ml of hydrochloric acid of 31 weight % strength. The whole was stirred for 15 minutes and then admixed with a further 662 ml of water and 8 mols of a 10 weight % solution of dibutylated naphthalene sulfonate (LEONIL DB, this is a registered Trade Mark of Hoechst Aktiengesellschaft, Frankfurt/M., Federal Republic of Germany). The suspension so obtained was continuously introduced within 1 hour into the base portion of the diazotization vessel (2) which was 4 cm wide and 70 cm high. At the same time, the diazotization vessel (2) was fed with sodium nitrite solution, through inlets (8, 9 and 10). A temperature of 10° C. was maintained inside the diazotization vessel (2) by cooling with brine. The conversion rate was 93% under these conditions. Unreacted 4-chloro-2-nitraniline was cycled as described in Example 3. The diazonium salt solution obtained downstream of the filter was post-diazotized in sojourn vessel (14) with a small quantity of sodium nitrite solution to effect reaction of dissolved amine.

We claim:

1. In a process for the continuous diazotization of primary aromatic amines by reacting a suspension of the amine in aqueous mineral acid with an aqueous sodium nitrite solution, the improvement which comprises: supplying continuously the lower portion of a cylindrical diazotization zone placed in upright position with an aqueous mineral acid suspension of a diazotizable primary aromatic amine and supplying the vessel simultaneously, via one or more inlets arranged one above the other so as to open laterally thereinto, with an aqueous sodium nitrite solution, the amine and nitrite being used in stoichiometric proportions, or the nitrite being used in a stoichiometric deficiency and the acid being used in an excess of about 1 to 3 equivalents per amine equivalent in the mineral acid suspension; reacting the resulting mixture with agitation and cooling and while producing a laminar flow of liquid matter at temperatures of about 5° to 30° C., the reaction mixture resulting from readily diazotizable amines being allowed to remain in the diazotization zone over a period of about 1 to 10 minutes, and that resulting from difficultly diazotizable amines being allowed to remain in the diazotization zone over a period of about 10 to 30 minutes; removing reaction mixture, in accordance with the diazotization velocity of the particular amine used, from the upper portion of the diazotization zone at a place where the reaction mixture is substantially free from nitrous acid, said place being situated in said zone at a level which is the higher the lower the diazotization velocity of the amine used; filtering the reaction mixture removed and delivering diazonium salt-containing solution to a sojourn zone.

2. A process as claimed in claim 1, wherein amines of high diazotization velocity are diazotized by introducing the aqueous sodium nitrite solution into the diazotization zone through the lowermost inlet opening thereinto.

3. A process as claimed in claim 1, wherein amines of reduced diazotization velocity are diazotized by introducing the aqueous sodium nitrite solution through a plurality of inlets opening into the diazotization zone, the sodium nitrite solution being admitted through the individual inlets in quantities decreasing from above to below so as to have a minor excess proportion of nitrous acid just in the reaction mixture formed within the region of the uppermost inlet.

4. A process as claimed in claim 1, wherein amines of reduced diazotization velocity are diazotized by introducing, into the reaction zone, a stoichiometric deficiency, with respect to the amine, of aqueous sodium nitrite solution, filtering off unreacted amine from the reaction mixture removed from the diazotization zone, and recycling the filter residue to the diazotization zone.

5. A process as claimed in claim 1, wherein the diazotization is effected at a temperature of 10° to 20° C.

6. A process as claimed in claim 1, wherein the reaction mixture contains, at the discharge place from the diazotization zone, some minor excess proportion of nitrous acid recognizable by spot reaction on potassium iodide starch paper.

7. A process as claimed in claim 1, wherein reaction mixture containing unreacted amine is post-diazotized in the sojourn zone by admixing it with aqueous sodium nitrite solution.

8. A process as claimed in claim 1, wherein the quality of the diazonium salt solution and azo dyestuffs made therefrom is influenced in reproducible manner by varying the residence time of the reaction mixture in the sojourn zone.

* * * * *